US011241453B2

(12) United States Patent
Eutick

(10) Patent No.: US 11,241,453 B2
(45) Date of Patent: Feb. 8, 2022

(54) ARSENIC COMPOSITIONS

(71) Applicant: Eupharma Pty Ltd, Northbridge (AU)

(72) Inventor: Malvin Eutick, Northbridge (AU)

(73) Assignee: Eupharma Pty Ltd, Northbridge (AU)

( * ) Notice: Subject to any disclaimer, the term of this patent is extended or adjusted under 35 U.S.C. 154(b) by 0 days.

(21) Appl. No.: 16/465,693

(22) PCT Filed: Aug. 2, 2017

(86) PCT No.: PCT/AU2017/050807
§ 371 (c)(1),
(2) Date: May 31, 2019

(87) PCT Pub. No.: WO2018/098519
PCT Pub. Date: Jun. 7, 2018

(65) Prior Publication Data
US 2020/0016196 A1  Jan. 16, 2020

(30) Foreign Application Priority Data

Dec. 1, 2016 (AU) .................... 2016904945

(51) Int. Cl.
*A61K 33/36* (2006.01)
*A61K 9/00* (2006.01)
*A61K 9/16* (2006.01)
*A61K 9/20* (2006.01)
*A61K 9/48* (2006.01)

(52) U.S. Cl.
CPC ............ *A61K 33/36* (2013.01); *A61K 9/0053* (2013.01); *A61K 9/16* (2013.01); *A61K 9/20* (2013.01); *A61K 9/48* (2013.01)

(58) Field of Classification Search
CPC combination set(s) only.
See application file for complete search history.

(56) References Cited

U.S. PATENT DOCUMENTS

| 2,080,004 | A | 5/1937 | Dearborn |
| 3,280,046 | A | 10/1966 | Hatch |
| 2004/0146573 | A1 | 7/2004 | Warrell, Jr. et al. |
| 2009/0246291 | A1 | 10/2009 | Burger et al. |

FOREIGN PATENT DOCUMENTS

| CN | 1471925 A | 2/2004 |
| EP | 1621077 A1 | 2/2006 |
| WO | 2004032822 A2 | 4/2004 |
| WO | 2006121280 A1 | 11/2006 |
| WO | 2011086193 A1 | 7/2011 |
| WO | 2016119019 A1 | 8/2016 |
| WO | 2016123603 A2 | 8/2016 |

OTHER PUBLICATIONS

Antman, "Introduction: The History of Arsenic Trioxide in Cancer Therapy," The Oncologist, vol. 6, Supp. 2, 2001, pp. 1-2.
Chen et al., "From an old remedy to a magic bullet: molecular mechanisms underlying the therapeutic effects of arsenic in fighting leukemia," Blood, vol. 117, No. 24, Jun. 16, 2011, pp. 6425-6437.
Gibaud et al., "Arsenic-Based Drugs: From Fowler's Solution to Modern Anticancer Chemotherapy," Topics in Organometallic Chemistry, vol. 32, 2010, pp. 1-20.
Zhu et al., "How acute promyelocytic leukaemia revived arsenic," Nature Reviews Cancer, vol. 2, No. 9, Sep. 2002, pp. 705-714.
International Patent Application No. PCT/AU2017/050807, International Search Report and Written Opinion dated Aug. 22, 2017, 9 pages.
Australian Patent Application No. 2016904945, International-Type Search Report dated Jun. 28, 2017, 10 pages.
EP Pat. App. No. 17876251.4, Extended European Search Report dated Jun. 23, 2020, 6 pages.
Sheldrick et al., "Zur Kenntnis van Natriumarseniten im Dreistoffsystem Na2O—As2O3—H2O bei 6°C," Zietschrift Fur Anorganische Und Allgemeine Chemie, vol. 549, No. 6, Jun. 1, 1987, pp. 177-186, English Abstract Submitted.
Wood et al. (2002) A Raman spectroscopic study of arsenite and thioarsenite species in aqueous solution at 25 C, Geochem. Trans, 3(4), pp. 31-39.
Roman-Ross et al. (2006) Arsenite sorption and co-precipitation with calcite, Chemical Geology, vol. 233, 328-336, 26 pgs.
Han M-J et al. (2007) Direct Evidence of Arsenic(lll)-Carbonate Complexes Obtained Using Electrochemical Scanning funneling Microscopy, Anal. Chem. 79, pp. 3615-3622.

*Primary Examiner* — Jennifer A Berrios
(74) *Attorney, Agent, or Firm* — Fredrikson & Byron, P.A.

(57) ABSTRACT

The present invention is predicated on the realisation that problems with the poor water solubility of arsenic trioxide and the extreme difficulty in dissolving arsenic trioxide in anything other than a very basic solution, could be overcome by forming a much more soluble diarsenic tetraoxide, including the compound $NaHAs_2O_4$, prior to its delivery to a patient. Pharmaceutical compositions with such compounds and their use in the treatment of cancers is disclosed.

17 Claims, 5 Drawing Sheets

ARSENIC COMPOSITIONS

This application is a 35 U.S.C. 371 national phase filing from International Application No. PCT/AU2017/050807, filed Aug. 2, 2017, which claims the benefit of Australian Patent Application No. 2016904945, filed on Dec. 1, 2016. The entire contents of these applications are incorporated herein by reference.

FIELD OF THE INVENTION

The invention relates to the field of metal-containing compounds and their use in the treatment of cancers. More particularly, this invention relates to arsenic containing compounds and their use in the treatment of cancers.

BACKGROUND TO THE INVENTION

Any reference to background art herein is not to be construed as an admission that such art constitutes common general knowledge in Australia or elsewhere.

Acute promyelocytic leukaemia (APL) and related cancers have been treated with arsenic trioxide in the form of a sterile IV infusion with dilution of a concentrated IV 10 mg/10 mL solution of arsenic trioxide into an infusion bag containing sterile water, saline or glucose and the patient given the arsenic trioxide by slow infusion.

Since arsenic trioxide is only sparingly soluble in water at physiological or acidic pH arsenic trioxide is typically solubilised in an aqueous solution at high pH, such as a pH greater than 12. Stirring and heating are required to solubilise all of the arsenic trioxide and achieve a clear solution. The solution is then too basic to be useful as a pharmaceutical composition and so must be first diluted in water, for example, to a concentration of about 1 mg/mL, pH 12. The arsenic trioxide solution is then adjusted with hydrochloric acid with constant stirring until the pH is 8.0 to 8.5, or lower if desired. The partially neutralized arsenic trioxide solution is then sterilised and packaged.

This sterile IV formulation has a number of drawbacks. Firstly, it must be prepared by aseptic addition of the 1 mg/mL solution into a sterile infusion bag. Secondly, the form of delivery is by slow infusion of the dilute IV bag, hence a patient must spend a number of hours in hospital on a considerable number of occasions during the induction and maintenance treatment phases over an intermittent period of about 4 to 6 months. This is a considerable drain on the patients, their families, the hospital resources and medical staff's time.

There is therefore a need for an improved formulation to deliver an active arsenic species useful in the treatment of a number of forms of cancer.

SUMMARY OF INVENTION

According to a first aspect of the invention, there is provided a pharmaceutical composition comprising a diarsenic tetraoxide and a pharmaceutically acceptable excipient.

Suitably, the diarsenic tetraoxide is an alkali metal and/or an alkaline earth metal diarsenic tetraoxide.

In one embodiment, the diarsenic tetraoxide comprises an $HAs_2O_4^-$ ion.

In embodiments, the diarsenic tetraoxide is of the formula $MHAs_2O_4$ wherein M is a metal of suitable valency.

Therefore, in one embodiment, the invention relates to a pharmaceutical composition comprising a diarsenic tetraoxide of the formula $MHAs_2O_4$ wherein M is a metal of suitable valency, and a pharmaceutically acceptable excipient.

In preferred embodiments, the diarsenic tetraoxide is of the formula $NaHAs_2O_4$.

Preferably, the diarsenic tetraoxide is present in solid form.

In one embodiment, the composition further comprises one or more of a drying agent, a disintegrant and a dispersant.

According to a second aspect of the invention there is provided a method of treating a cancer in a patient including the step of orally administering a diarsenic tetraoxide to the patient to thereby treat the cancer.

A third aspect of the invention resides in a diarsenic tetraoxide for use in treating a cancer in a patient.

A fourth aspect of the invention resides in a diarsenic tetraoxide for use in the manufacture of a medicament for the treatment of cancer in a patient.

In certain embodiments of the second, third and fourth aspects, the cancer is selected from a haematological malignancy, a solid tumour and a lymphoma.

Preferably, the cancer is selected from acute promyelocytic leukaemia (APL) and multiple myeloma.

In certain embodiments of the second, third and fourth aspects, the diarsenic tetraoxide is administered in solid form.

The diarsenic tetraoxide of the second, third and fourth aspects, may be as described for the first aspect. The diarsenic tetraoxide may be administered as part of the pharmaceutical composition of the first aspect.

A fifth aspect of the invention resides in a method of delivering a therapeutically effective amount of arsenic to a patient including the step of administering to the patient an amount of a diarsenic tetraoxide.

Suitably, administration is oral administration of a solid form of diarsenic tetraoxide which may be as described for the first aspect.

The various features and embodiments of the present invention, referred to in individual sections above apply, as appropriate, to other sections, mutatis mutandis. Consequently features specified in one section may be combined with features specified in other sections as appropriate.

Further features and advantages of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein.

DETAILED DESCRIPTION

Figure 1:
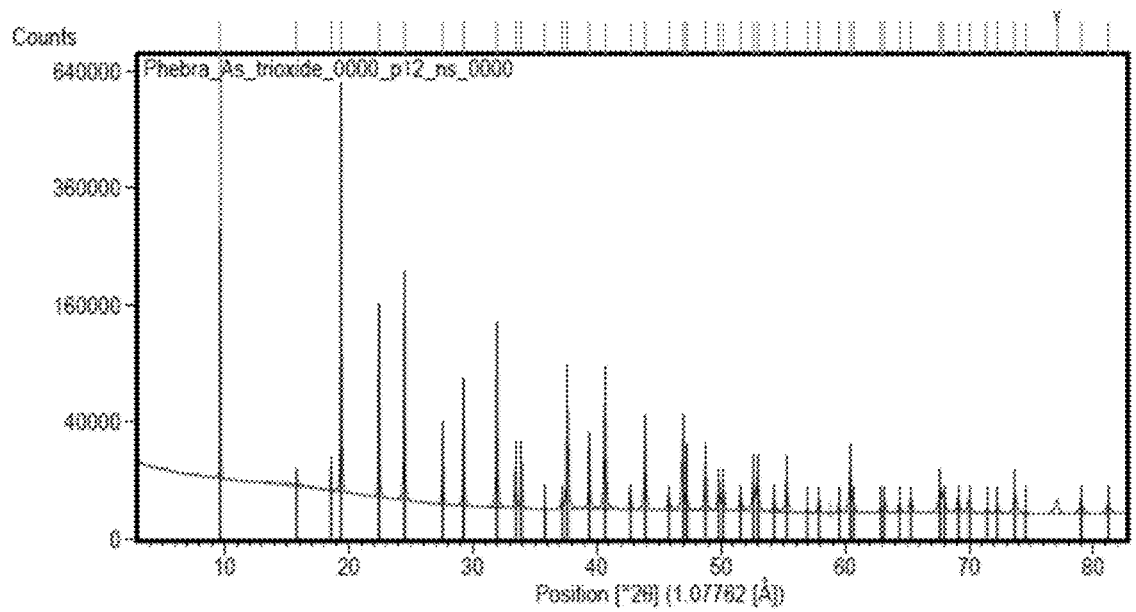
FIG. 1 is an X-ray powder diffraction pattern for a control $As_2O_3$ sample with the overlayed search match results.

In a broad form, it has been found that a diarsenic tetraoxide, which in the body provides an active oxide of arsenic III, has a substantially different solubility profile to arsenic trioxide, typically used in treatment of certain cancers to deliver the active arsenic ion, in that the arsenic trioxide is extremely difficult to dissolve except at high pH. The present diarsenic tetraoxide has been demonstrated experimentally herein to dissolve in less than 10 seconds at pH about 1 and in well under a minute in pH 7.

The present invention is therefore predicated, at least in part, on the realisation that problems with the poor water solubility of arsenic trioxide and the extreme difficulty in dissolving arsenic trioxide in anything other than a very basic solution, could be overcome by forming a much more soluble diarsenic tetraoxide, preferably $NaHAs_2O_4$, compound prior to its delivery to a patient. The typical solution to the solubility issue has been to dissolve the arsenic trioxide in a solution of sodium hydroxide and then to adjust the pH of this solution down to pH 6 to 8, to be better suited for delivery to patients in a liquid form. The use of concentrated acid has always been avoided due to concerns over the precipitation of the arsenic trioxide from solution.

It has now been found that $NaHAs_2O_4$ can be very rapidly dissolved in stomach acid without any precipitation of an arsenic compound. This goes against conventional wisdom which teaches that the strongly acidic gastric juices should cause a precipitation of arsenic trioxide from solution almost immediately after the salt dissolves. This finding allows the oral delivery of an arsenic III ion, as an effective arsenic trioxide equivalent, to the sterile IV product in a convenient solid form which can be manufactured in the form of a tablet, suppository, granule or, preferably, capsule. There has been a long felt need for such a delivery option since it can greatly reduce the amount of time a patient needs to spend in hospital, particularly during the maintenance phase of treatment. This is an improvement for the patient and a substantial cost saving in terms of hospital resources.

Prior to this point a number of well documented attempts over a long time period have been made to find a solid form of arsenic trioxide which could be delivered orally. The use of salt and/or particle micronisation, wetting or surfactant agents, strong dispersants such as citric acid and other approaches were all trialled unsuccessfully. Recently, lyophilizing the arsenic trioxide solution has been attempted.

A further deterrent to the use of a solid oral form of arsenic trioxide is that to achieve acceptable bioavailability the arsenic trioxide must be dissolved within the stomach in less than about 20 minutes and preferably less than about 10 minutes. This is because the absorption of the arsenic III ion of arsenic trioxide occurs in the distal part of the small intestine and gastric emptying, on a stomach containing about 250 mL of liquid, occurs in a little over 23 minutes.

The pH of the gastric juices on an empty stomach would be approximately pH 1 to 2 and so is strongly acidic. On discharge to the distal small intestine the pH increases to >pH6 and thus dissolution of any undissolved solid salt may be slow or retarded.

This means that any oral delivery form of arsenic trioxide must be soluble at pH 1 to 2 within a maximum time frame of 20 minutes, preferably significantly less, to ensure complete delivery of the solubilised arsenic trioxide dose in a timely and predictable manner. This dissolution time frame cannot be met with the use of solid arsenic trioxide which is only slightly soluble at neutral pH and while it is considered to be more soluble at acid pH, has been found to be still a very slow process even in vitro with strong stirring at low pH (see later experimental section). However, the effective dissolution of $NaHAs_2O_4$ in gastric juices within the 20 minute timeframe has allowed this challenge to be successfully addressed while still delivering the desired active arsenic three cation which is that delivered via the IV route. The complete dissolution in gastric juices of $NaHAs_2O_4$ has been shown to occur in less than 1 min and even less than 30 seconds. This extremely short timeframe cannot be attained even with solid salt forms of the soluble meta salts of arsenic such as sodium or potassium meta arsenites.

Importantly, the strongly alkaline nature of the $NaHAs_2O_4$ and presence of sodium carbonate and/or sodium bicarbonate in the employed compositions, causes a very rapid bubbling and turbulent effervescence causing dissolution of the powder and dispersal of the salt, as the arsenic (III) cation, in the acid of the gastric fluid. The reaction is very fast, as is shown in the experimental section. Importantly, when compared to a salt like sodium meta arsenite, which will also dissolve although more slowly as shown in the experimental section, the strong acid/strong alkali reaction causes a turbulent fizzing and bubbling effect which effervescence assists in mixing the arsenic ion in the gastric fluid.

It should be appreciated then that the $NaHAs_2O_4$ in an orally deliverable composition has two key advantages over other arsenic salts, such as sodium meta arsenite, including: (i) significantly faster dissolution in the acidic conditions of the stomach (or even at neutral pH); and (ii) the explosive, bubbling effervescence of the highly alkaline but solid composition causes rapid mixing and dispersion in the stomach. The resultant mixture in the body is the active arsenic III cation, a sodium cation (if a sodium salt is employed), carbon dioxide and carbonic acid, all of which mimic the effect of receiving an alkali pre-dissolved arsenic trioxide injection. In essence this means the arsenic III cation dose provided by the compound and composition of the present invention is the same as if the patient was given an equivalent IV dose of arsenic trioxide and so the therapeutic effect on cancers and other disease processes is entirely predictable based on the already known efficacy of arsenic trioxide treatment. That is, the delivery form is more efficient but the end result in terms of active agents is exactly the same.

In this patent specification, adjectives such as first and second, left and right, front and back, top and bottom, etc., are used solely to define one element or method step from another element or method step without necessarily requiring a specific relative position or sequence that is described by the adjectives.

Unless defined otherwise, all technical and scientific terms used herein have the same meaning as would be commonly understood by those of ordinary skill in the art to which this invention belongs.

The term "dispersant" as used herein, refers to an agent which improves the separation of particles of the diarsenic tetraoxide from one another and thereby aids in improving the speed of dissolution of that salt in the stomach juices of a patient.

The term "treatment", as used herein in relation to the various cancers treated by the diarsenic tetraoxide, means that the disease and the symptoms associated with the disease are alleviated, reduced, cured, or placed in a state of remission.

According to a first aspect of the invention, there is provided a pharmaceutical composition comprising a diarsenic tetraoxide and a pharmaceutically acceptable excipient.

Suitably, the pharmaceutical composition comprises the diarsenic tetraoxide in solid form.

Preferably, the diarsenic tetraoxide is a diarsenic (III) tetraoxide.

Suitably, the diarsenic tetraoxide is an alkali metal and/or an alkaline earth metal diarsenic tetraoxide In one preferred embodiment the diarsenic tetraoxide may be selected from the group consisting of a sodium diarsenic tetraoxide, a potassium diarsenic tetraoxide, a magnesium diarsenic tetraoxide, an ammonium diarsenic tetraoxide and a calcium diarsenic tetraoxide.

Preferably, the diarsenic tetraoxide is a sodium diarsenic tetraoxide and more preferably a sodium diarsenic (III) terraoxide.

In embodiments, the diarsenic tetraoxide comprises an $HAs_2O_4^-$ ion.

This may be combined with a counter ion which may be selected from sodium, potassium, calcium and ammonium.

In embodiments, the diarsenic tetraoxide is of the formula $MHAs_2O_4$ wherein M is a metal of suitable valency. M may be selected from any metal with an appropriate valency. Preferably M is an alkali metal and/or an alkaline earth metal of suitable valency. Sodium and potassium are preferred metals.

Therefore, in one embodiment, the invention relates to a pharmaceutical composition comprising a diarsenic tetraoxide of the formula $MHAs_2O_4$ wherein M is a metal of suitable valency, and a pharmaceutically acceptable excipient.

In preferred embodiments, the diarsenic tetraoxide is of the formula $NaHAs_2O_4$.

Preferably, the diarsenic tetraoxide of any of the embodiments described herein is present in solid form.

In one embodiment, the composition further comprises one or more of a drying agent, a disintegrant and a dispersant.

The diarsenic tetraoxide may be a salt formed by dissolution of arsenic trioxide in a solution of a hydroxide of an alkali metal and/or an alkaline earth metal and reacted with a carbonate compound prior to mixing with a bicarbonate. Arsenic trioxide is known to only be soluble in aqueous solutions at high pH, for example above about pH 12, and so only solutions of strong bases such as those formed by hydroxides of alkali metals and/or alkaline earth metals are likely to be suitable. However, potentially any strong base, for example ammonium hydroxide, may be used to dissolve the arsenic trioxide and thus may be suitable.

In one embodiment the hydroxide of an alkali metal and/or an alkaline earth metal may be selected from the group consisting of sodium hydroxide, potassium hydroxide, magnesium hydroxide, calcium hydroxide, lithium hydroxide, rubidium hydroxide, strontium hydroxide, barium hydroxide, and caesium hydroxide. These hydroxides are all known to form strongly basic aqueous solutions. Due to the nature of the counter ion some of these hydroxides may be less favoured than others. For example, some lithium salts may be physiologically less preferred. The use of sodium hydroxide to form the strongly basic solution in which the arsenic trioxide is dissolved is particularly preferred due to the current clinical use of a pH adjusted solution of sodium hydroxide containing arsenic trioxide for IV delivery. This has shown that IV use of a sodium hydroxide solution of arsenic trioxide is both safe, within the known degrees of arsenic toxicity, and effective in treating cancers.

In another embodiment the hydroxide may be ammonium hydroxide.

The composition may further comprise a drying agent, a disintegrant or dispersant. The drying agent, disintegrant or dispersant may be effervescent. In one embodiment, the drying agent, disintegrant or dispersant is a bicarbonate and/or a carbonate. Suitably, the disintegrant or dispersant is one or more selected from the group consisting of sodium bicarbonate, sodium carbonate, potassium carbonate, potassium bicarbonate, calcium carbonate, magnesium carbonate and magnesium bicarbonate, and combinations thereof.

The disintegrant or dispersant contributes to the fast dissolution of the diarsenic tetraoxide in the gastric juices. The use of an effervescent disintegrant or dispersant, such as the bicarbonates or carbonates of alkali metals or alkaline earth metals, is particularly effective upon contacting the gastric juices as there is an immediate and turbulent fizzing reaction which acts to effectively separate the particles of the diarsenic tetraoxide to put them into solubilised ionic form.

In one embodiment, the diarsenic tetraoxide is not one which which is formed without the use of a hydrogen carbonate, such as sodium hydrogen carbonate. That is, the contacting of the reaction mixture or substrates with a hydrogen carbonate, such as sodium hydrogen carbonate, is necessary for formation of the diarsenic tetraoxide product.

The composition may be in the form of a tablet, suppository, granule or capsule. Any pharmacologically acceptable vehicle for the diarsenic tetraoxide may be acceptable so long as it does not interact with the diarsenic tetraoxide and does not impede the dissolution in the stomach. Capsules which are currently used for the delivery of actives to the stomach for rapid dissolution are considered particularly appropriate for use with the present composition, not least as the patient or medical staff will not come into direct contact with the arsenic compound during handling. Gelatin capsules are one example of such capsules. The composition may be in the form of a powder or granules within the tablet or capsule. Depending on the method of drying down of the solvent to form the diarsenic tetraoxide, crystalline salts may even be provided. The solid formed may be further pulverised or micronized or otherwise treated to reduce the particle size if required to provide even faster dissolution.

The excipient may be any appropriate pharmaceutically acceptable excipient. In one embodiment, the drying agent, disintegrant and the excipient may be one and the same.

According to a second aspect of the invention there is provided a method of treating a cancer in a patient including the step of orally administering an diarsenic tetraoxide to the patient to thereby treat the cancer.

A third aspect of the invention resides in a diarsenic tetraoxide for use in treating a cancer in a patient.

A fourth aspect of the invention resides in a diarsenic tetraoxide for use in the manufacture of a medicament for the treatment of cancer in a patient.

In certain embodiments of the second, third and fourth aspects, the diarsenic tetraoxide is administered in solid form.

In relation to the second, third and fourth aspects, in one embodiment the cancer is a haematological malignancy. In one embodiment the cancer is a leukaemia, multiple myeloma, a solid tumour or a lymphoma.

The cancer may be selected from the group consisting of squamous cell carcinoma, basal cell carcinoma, melanoma tumours of the epithelial lining of glands or ducts, adenocarcinoma, myelodysplastic syndrome (MDS), papillary carcinoma, papillary adenocarcinoma tumours of the liver and biliary tract, epatocellular carcinoma tumours of the gastrointestinal tract, squamous cell carcinoma of the esophagus, adenocarcinoma of the esophagus, colorectal carcinoma (colon cancer), gastric carcinoma (stomach cancer) tumours of the respiratory tract, bronchogenic carcinoma, small cell carcinoma, large cell carcinoma tumours of the urogenital tract, transitional cell carcinomas of the bladder, squamous cell carcinoma of the bladder, carcinoma of the prostate, carcinoma of the cervix, blood cells and related cells (leukemias), acute and chronic lymphocytic leukaemia, polycythemia vera, cancers of lymphoid tissue, malignant lymphomas including Hodgkin's lymphoma and non-Hodgkin's lymphoma, follicular lymphoma, diffuse lymphoma, small lymphocytic lymphoma, large cell lymphoma, lymphoblastic lymphoma, multiple myeloma, tumours of connective tissue, cancers of bone osteosarcoma, tumours of the nervous system, neuroblastoma, retinoblastoma, glioblastoma, oligodendroglioma tumours associated with oncogenic viruses, burkitts lymphoma, b cell lymphoma's in immuno-comprised individuals, nasopharyngeal carcinoma and hepatitis b virus hepatocellular carcinoma.

When the cancer is leukaemia it may be a form selected from the group consisting of acute lymphoblastic leukaemia (ALL), acute lymphoblastic B-cell leukaemia, acute lymphoblastic T-cell leukaemia, acute myeloblastic leukaemia (AML), acute promyelocytic leukaemia (APL), acute monoblastic leukaemia, acute erythroleukemic leukaemia, acute megakaryoblastic leukaemia, acute myelomonocytic leukaemia, acute undifferentiated leukaemia, chronic myelocytic leukaemia, myelodysplastic syndrome (MDS) and chronic lymphocytic leukaemia.

Preferably, the cancer is acute promyelocytic leukaemia (APL).

When the cancer is a solid tumour it may one or more of cancer of the digestive tract, oesophagus, liver, stomach, colon, skin, brain, bone, breast, lung and soft tissues, including various sarcomas and prostate cancer.

The cancer may be any cancer which is currently indicated for treatment by clinically available arsenic trioxide solutions or against which solutions of arsenic trioxide have been shown to demonstrate efficacy.

In one embodiment, the lymphoma, leukaemia or solid tumour in the patient is refractory to standard methods of treatment, or is a relapsed case of leukaemia.

The diarsenic tetraoxide may be used alone or in combination with a further anti-cancer agent including wide range of known therapeutic agents such as, for example, immunotherapeutics, monoclonal antibodies, chemotherapeutics, small molecule actives such as melatonin and ATO in hepatic cancer, and valproate and sodium phenoxybutyrate with ATO in MDS, radioprotectants and radiotherapeutics. Particularly, the oral delivery of the diarsenic tetraoxide may occur before, during or after the administration of one or more known antitumor agents including but not limited to mustard compounds, nitrogen mustard, chlorambucil, melphalan, cyclophosphamide, 6-mercaptopurine, 6-thioguanine, cytarabine, 5-fluorouracil, floxuridine, methotrexate, vincristine, vinblastine, taxol, etoposide, temiposide, dactinomycin, daunorubicin, doxorubicin, bleomycin, mitomycin, cisplatin, carboplatin, estramustine phosphate, hydroxyurea, BCNU, procarbazine, VM-26, interferons, and all-trans retinoic acid (ATRA), or other retinoids.

The therapeutic dose and dosing frequency of the diarsenic tetraoxide in the treatment of various cancers will depend on the nature of the cancer, the severity of the condition as well as age, body weight, condition and response of the individual patient. Importantly, such dosing can conveniently be decided upon based on standard processes and following the guidelines of current dosing regimens for IV delivery of arsenic trioxide. This is based upon the understanding that the present use of a diarsenic tetraoxide is effectively a more advantageous means by which to provide, to a patient, a therapeutic bioequivalence of arsenic trioxide and the active species derived therefrom in the body. The therapeutic effect obtained and therefore efficacy of the treatment will be substantially as is observed for treatment of cancers using arsenic trioxide. Studies on the use and activity of arsenic trioxide in treating a range of cancers are freely available in the scientific and medical literature. Thus, for specific cancers, the already developed dosing and toxicity protocols for clinically available arsenic trioxide by IV delivery can be used. In one embodiment, a daily dose of between 0.05 to 5.0 mg/kg/day may be suitable for delivery to a patient requiring induction therapy. A preferred dose may be about 0.15 mg/kg/day.

The present diarsenic tetraoxide is advantageous in that delivery of such an oral form versus IV injection of dissolved arsenic trioxide means that approximately the same dose of the arsenic three cation is achieved in the patient's body over a 24 hour period but the oral form has an advantage in that the peak concentrations of the ion do not reach those of the injection and it is generally accepted that this will mean fewer adverse drug reactions, especially cardiac complications.

The patient being treated for the cancer will be a human in need of such arsenic trioxide therapy.

The diarsenic tetraoxide, of the second, third and fourth aspects, is as described for the first aspect. The diarsenic tetraoxide may be administered as part of the pharmaceutical composition of the first aspect. Preferably, the diarsenic tetraoxide is $NaHAs_2O_4$ with amounts of sodium bicarbonate and/or sodium carbonate in the composition. This solid composition can then be taken orally by the patient, preferably in the form of a capsule or tablet containing the composition.

A fifth aspect of the invention resides in a method of delivering a therapeutically effective amount of arsenic to a patient including the step of administering to the patient an amount of a diarsenic tetraoxide.

Suitably, the administration is oral administration of a solid form of diarsenic tetraoxide. The diarsenic tetraoxide may be as described for the first aspect.

The method of the fifth aspect may be performed in keeping with any of the embodiments described for the first to the fourth aspects.

EXPERIMENTAL

Preparation of Diarsenic Tetraoxide Salt—$NaHAs_2O_4$

References to the various materials in the synthesis of the diarsenic tetraoxide salt which follow, relate to the amounts of those materials set out in table 1. References to vessels such as a mortar will be understood by a person of skill in the art to relate to the scale of synthesis and suitable larger scale vessels would be apparent to said person for scaled up synthesis.

Transfer all of the arsenic trioxide followed by the sodium hydroxide and then the water, an amount suitable for irrigation, into a suitably sized mortar. Ensure the materials are fully mixed by gently swirling the mortar and leave to stand until the materials are fully dissolved. The mortar and contents will become hot.

Once the material has fully dissolved, transfer all of the sodium carbonate to the mortar. Ensure the sodium carbonate is fully wetted with no visible dry pockets. Leave to cool to room temperature which typically takes a minimum of 1 hr. Next, transfer all of the sodium hydrogen carbonate (sodium bicarbonate) to a stainless steel tray and then transfer the cooled contents of the pestle and mortar on to the tray and use a small portion of the dispensed sodium hydrogen carbonate to wash out the mortar. Manually disperse the cooled sodium carbonate/arsenic trioxide/sodium hydroxide mixture in the sodium hydrogen carbonate on the stainless steel tray.

Set up a 2000 μm sieve on a second stainless steel tray. Pass the bulk material through the sieve. If any material has adhered to the sieve and is blocking holes within the sieve, pass the bulk material back through the sieve until they are clear (any blocking is caused by locally over-wet material, passing the bulk through will re-distribute the water through the blend reducing the water content of the material blocking the sieve which will then pass through the sieve). This operation can be repeated until all the material has been removed from the sieve.

Carefully transfer the manufactured wet mass from the stainless steel tray to a polyethylene bag, weigh and calculate the wet mass yield. The yield should preferably be between 97%-101%. Drying will take place to a constant weight, defined as an LOD change of <2% from the previous weighing. An assay sample should be taken at the constant weight point. The assay result will be used to confirm the end point of drying.

Open the bag and spread the wet mass evenly over both stainless steel trays. Place each tray in the vacuum oven set at 40° C. Dry with an applied vacuum greater than 850 mbar for a minimum of 24 hours before taking the first weighing. Each subsequent weighing should be taken at 2 hour drying intervals. The drying is considered complete when the % LOD for each subsequent weighing is unchanged.

Set up a 355 μm sieve on top of a blender drum and pass the previously dried material through the sieve into the blender drum. Any material that does not pass through the sieve should be milled with the pestle and mortar to a particle size which will then pass through the 355 μm sieve. Once all the material has been passed through the sieve into the blender drum remove the sieve and the final product, $NaHAs_2O_4$, is ready for loading into white hard gelatin capsules.

The above process can be scaled up for bulk manufacture, as desired. For example, table 2 indicates amounts for a batch production.

TABLE 1

Master formula with materials and amounts to form diarsenic tetraoxide salt.

| Material | Quantitative Formula for encapsulation (% w/w) | Unit Formula |
|---|---|---|
| Arsenic Trioxide | 1.89 | 5 mg |
| Sodium Carbonate | 9.43 | 25 mg |
| Sodium Hydrogen Carbonate | 87.17 | 231 mg |
| Sodium Hydroxide | 1.51 | 4 mg |
| Total | 100% | 265 mg |

TABLE 2

Batch formula with materials and amounts to form the diarsenic tetraoxide salt $NaHAs_2O_4$.

| Material | Quantitative Formula for encapsulation (% w/w) | Batch size 2887.6 g (2782.5 g dried blend) |
|---|---|---|
| Arsenic Trioxide | 1.82 | 52.6 |
| Sodium Carbonate | 9.09 | 262.5 |
| Sodium Hydrogen Carbonate | 84.00 | 2425.6 |
| Sodium Hydroxide | 1.45 | 41.9 |
| Water for irrigation** | 3.64 | 105.1 |
| White hard gelatin capsule | 1 capsule* | 10500 |
| Total weight (blend only) (H) | | 2782.5 g |

*Water for irrigation removed during process;
**number of capsules required = total blend weight (g)/nominal fill weight (g)

The above procedure was employed in two individual manufacturing runs to provide two separate amounts of $NaHAs_2O_4$ product (to ensure reproducibility) which were labeled 1a and 3. The procedure was also repeated, again in two separate experiments, but importantly without the step where the sodium carbonate/arsenic trioxide/sodium hydroxide mixture is combined with the sodium hydrogen carbonate. That is, the second procedure omitted the combining of the sodium hydrogen carbonate to assess the effect of this variation. The two samples thereby produced were labeled 1b and 2.

Characterisation of Arsenic Salts

These manufactured samples (1a to 3 were characterised along with arsenic trioxide and sodium meta arsenite as reference materials to show that clear distinctions existed between the samples and these controls and so to demonstrate the above procedure had indeed resulted in a conversion of the arsenic trioxide to a new species which was not a meta arsenite. Hence, six samples, being commercially obtained $As_2O_3$ and sodium meta-arsenite, sample 1a, sample 1 b, sample 2 and sample 3, were examined by synchrotron X-ray powder diffraction in the Powder Diffraction Beamline at the Australian Synchrotron. The objective of the investigation was to determine the phase assemblage of the as manufactured powders in sample 1a, sample 1 b, sample 2 and sample 3. The data sets from all the samples were assessed by the investigators to be of high quality. Prior to analysis, the powder samples were lightly ground in a mortar and pestle and packed into separate 0.3 mm diameter borosilicate capillaries. The packed capillaries were mounted individually on separate sample holders.

X-ray diffraction patterns for each sample were collected at the Powder Diffraction beamline (10BM-1) at the Australian Synchrotron [1] using X-rays of wavelength 1.07761 (1) Å. The diffracted X-rays were detected using a Mythen II Microstrip detector system [2]. Each sample-filled capillary was aligned and mounted in the centre of the diffractometer. Data was collected from a diluted LaB6 660b Standard Reference Material supplied by the National Institute of Standards and Technology (NIST, USA). The X-ray wavelength and zero offset were determined to be 1.07761(1) Å and −0.0017(1)° respectively after Rietveld refinement of the 660b data set. The capillaries were continually rotated during data collection to maximise powder averaging. Data acquisition times were 10 minutes per detector position per sample. Each sample required 20 minutes of data collection time (two detector positions) and the data were collected at ambient pressure and temperature. The acquired diffraction patterns were merged using the in-house software package PDViPeR (v2.0). The software program HighScore (v4.0), coupled with the ICDD PDF-4 database, was used to view the diffraction data and perform search/matching for phase identification.

Sections of the merged synchrotron X-ray powder diffraction data are shown in FIGS. 1 to 9. The intensity versus 2-theta data shows a series of peaks indicating distinct interplanar d-spacings within the crystallites. For each diffraction data pattern, the background was not subtracted, however it was modelled to assist the determination of the peak intensities. A peak search algorithm was used in the HighScore software program to identify the peaks present up to 60 degrees 2-theta. These peak positions were used to search the International Centre for Diffraction Data (ICDD) PDF-4 database to assist with the determination of phases present. The very low diffractometer zero offset allowed for the peak positions from each sample to be compared directly to the reference data in the ICDD PDF-4 database.

The X-ray powder diffraction data from all six powder samples had excellent signal-to-noise properties and showed good angular resolution. This high data quality significantly improves the ability to identify the phases present.

FIG. 1 shows the diffraction pattern for the $As_2O_3$ reference sample and the overlayed search match results. The ICDD PD-4 reference pattern 00-036-1490 [3] for arsenic trioxide exhibited good agreement with the data. The diffraction pattern from the $As_2O_3$ reference sample is shown in red. The green line shows the fitted background and the blue markers indicate the reference peak positions from PDF-4 reference pattern 00-036-1490. The good agreement and hence overlap between the as-collected data and the reference pattern indicate that the main phase is $As_2O_3$. No impurity peaks were observed.

Figure 2:
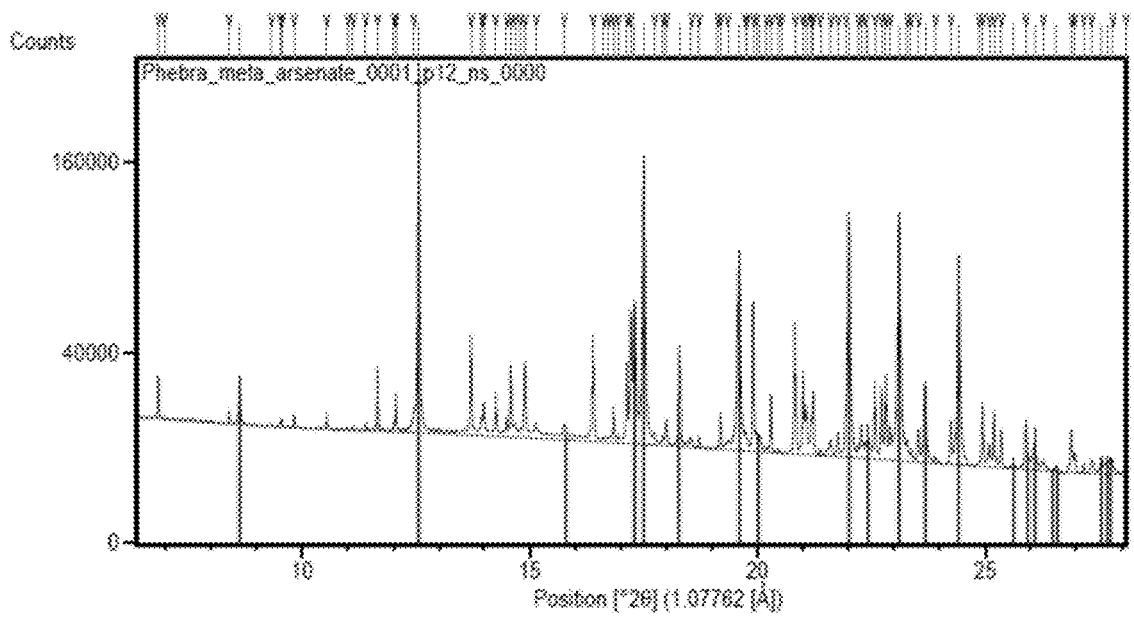
FIG. 2 is an X-ray powder diffraction pattern for a control sodium meta arsenite sample with the overlayed search match results.

FIG. 2 shows the diffraction pattern for the sodium meta-arsenite reference sample and the search/match results. The ICDD PDF-4 reference pattern 04-016-1771 [4] for sodium arsenite ($NaAsO_2$) agreed well with the data, although there were unmatched peaks indicating that one or more additional impurity phases were present in the sample. A segment of the diffraction pattern from the sodium meta-arsenite reference sample is shown in red from 6°-28° 2-Theta. The green line shows the fitted background and the blue markers indicate the reference peak positions from PDF-4 reference pattern 04-016-1771. Good agreement between the as-collected data and the reference pattern indicate that sodium meta-arsenite is the major phase.

Figure 3:
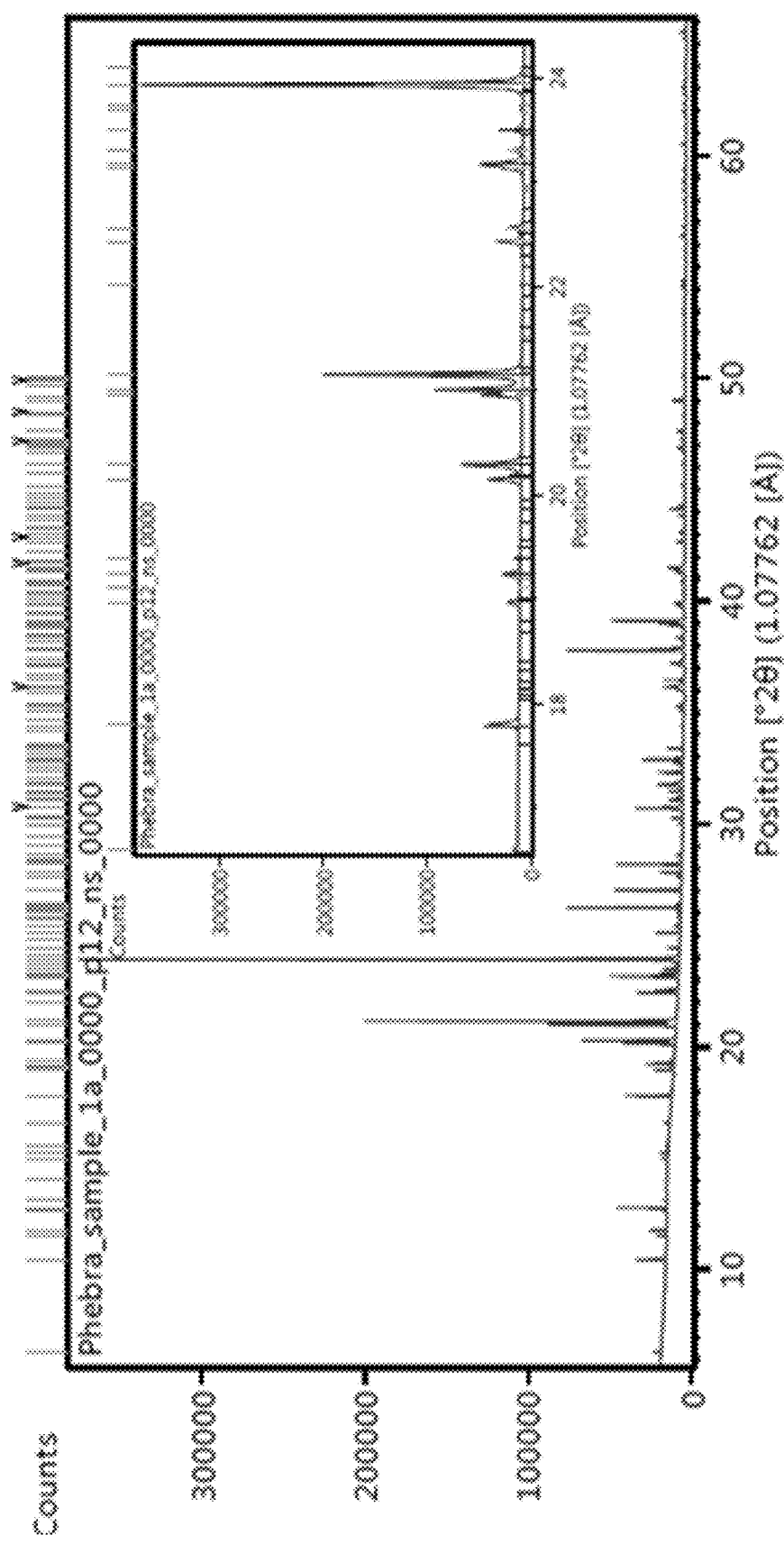
FIG. 3 is an X-ray powder diffraction pattern for sample 1a, being a diarsenic tetraoxide of the invention, with the overlayed search match results.

FIG. 3 shows the diffraction pattern for Sample 1a. The inset reveals the search/match results for a section of the data. The phases $Na(HCO_3)$ 04-017-3645 [5] and $Na_2CO_3.H2O$ 01-070-2148 [6] were identified as likely remnants of the manufacturing with sodium carbonate and bicarbonate with the phase $NaHAs_2O_4$ 04-011-6938 [9] being identified as a newly synthesised component as a result of the above described manufacturing process. A small number of unmatched peaks were observed indicating the presence of one or more minor impurity phases. The diffraction pattern from sample 1a is shown in red from 6°-65° 2-Theta. The green line shows the fitted background. The inset shows a segment of the data with the search/match results. Each colour line group indicates the presence of an identified phase.

Figure 4:
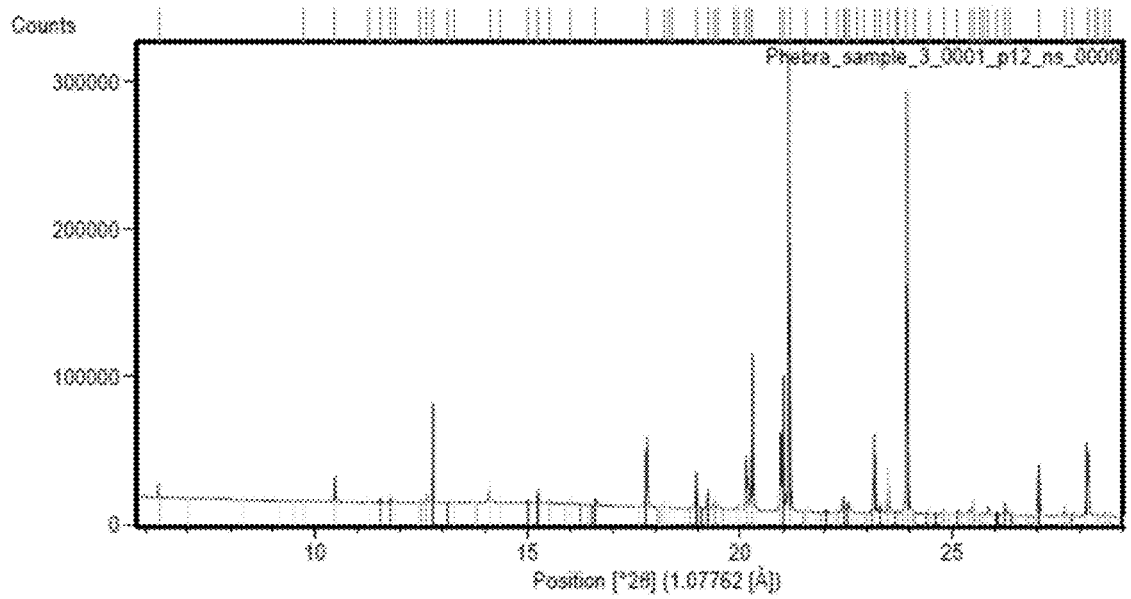
FIG. 4 is an X-ray powder diffraction pattern for sample 3, being a diarsenic tetraoxide of the invention, with the overlayed search match results.

FIG. 4 shows a section of the diffraction pattern and the search/match results for sample 3. Again, $Na(HCO_3)$ 04-017-3645 [5] was observed along with $Na_2CO_3.H_2O$ 01-070-2148 [6] as manufacturing remnants and $NaHAs_2O_4$ 04-011-6938 [9] was identified as a major component, once again verifying the above procedure as an effective method of synthesising a diarsenic tetraoxide salt via a transformation of arsenic trioxide. A segment of the diffraction pattern of sample 3 is shown in red from 6°-29° 2-Theta. The individual phases identified are indicated by a colour line group. $Na(HCO_3)$ (blue) was identified with $Na_3H(CO_3)_2.2H_2O$ (green), $Na_2CO_3.H_2O$ (pink) and $NaHAs_2O_4$ (yellow).

Figure 5:
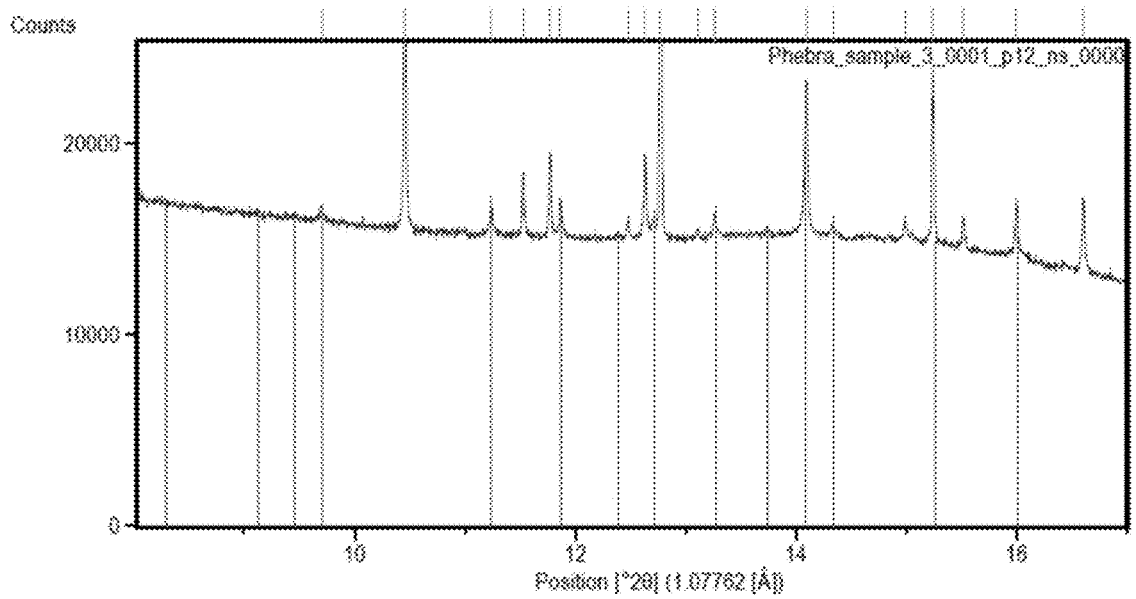
FIG. 5 is a magnified X-ray diffraction pattern from sample 3 from 8-17 degrees 2-Theta showing the peak matches for $HNaAs_2O_4$ phase (ICDD 04-011-6938)
Figure 6:
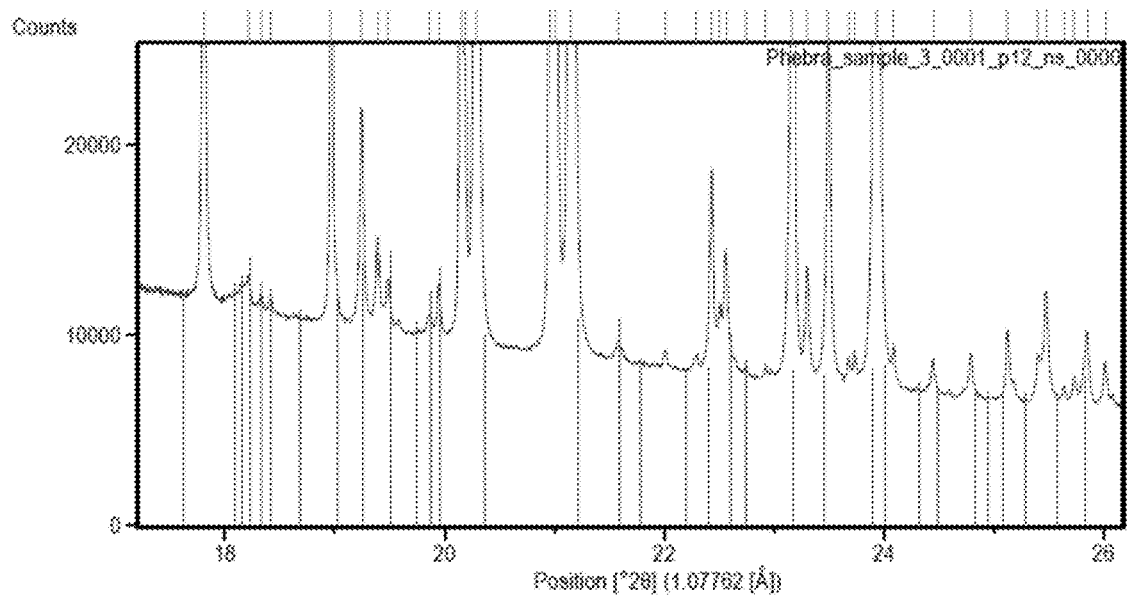
FIG. 6 is a magnified X-ray diffraction pattern from sample 3 from 17-26 degrees 2-Theta showing the peak matches for $HNaAs_2O_4$ phase (ICDD 04-011-6938)
Figure 7:
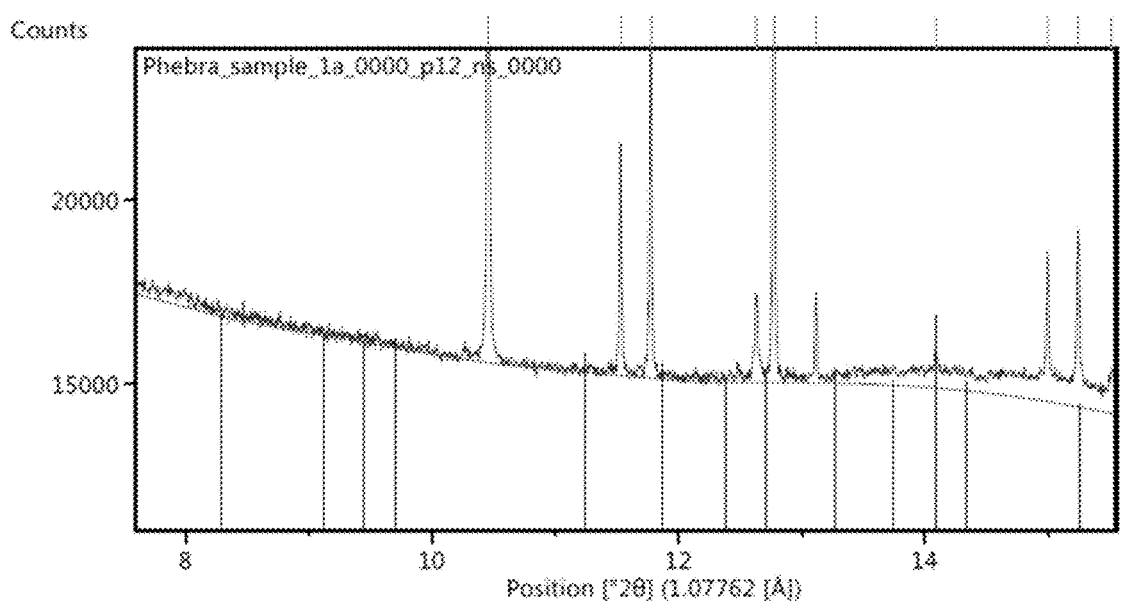
FIG. 7 is a magnified X-ray diffraction pattern from sample 1a from 8-15 degrees 2-Theta showing the peak matches for $HNaAs_2O_4$ phase (ICDD 04-011-6938)

FIG. 5 is a magnified X-ray diffraction pattern of sample 3 from 8-17 degrees 2-Theta specifically showing the peak matches for the $NaHAs_2O_4$ phase (ICDD 04-011-6938) while FIG. 6 is a magnified X-ray diffraction pattern from sample 3 from 17-26 degrees 2-Theta again demonstrating the peak matches for the $NaHAs_2O_4$ phase (ICDD 04-011-6938). The relative peak intensities for the $NaHAs_2O_4$ phase are restricted by limitations of the search/match software. FIG. 7 is a magnified X-ray diffraction pattern of sample 1a from 8-15 degrees 2-Theta specifically showing the peak matches for the $NaHAs_2O_4$ phase (ICDD 04-011-6938). Again, the relative peak intensities for the $NaHAs_2O_4$ phase are restricted by limitations of the search/match software.

Figure 8:
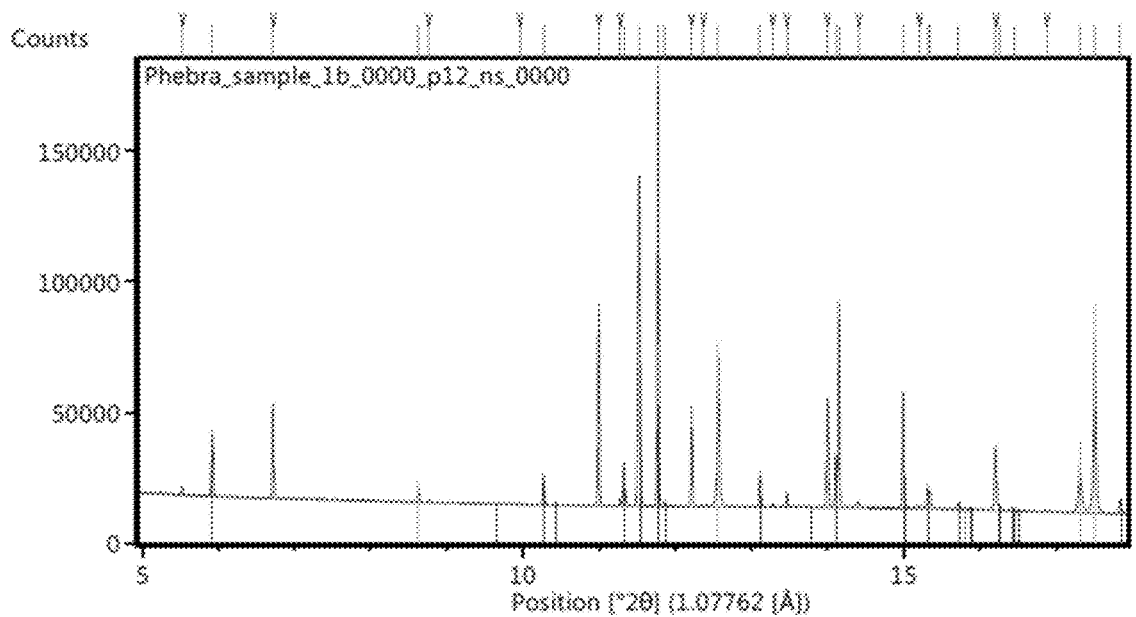
FIG. 8 is an X-ray powder diffraction pattern for sample 1 b, being a comparitor sample, from 5°-18° 2-Theta with overlayed search match results.

FIG. 8 shows a section of the diffraction pattern and the search/match results for sample 1 b, one of the two samples formed without the use of sodium hydrogen carbonate. The phases $NaAsO_2$ 04-016-1771 [4] and $Na_2CO_3.H_2O$ 01-070-2148 [6] were identified as being present at major levels. The phases $Na_2CO_3$ 00-019-1130 [8] and $Na_{6.26}(AsO_4)_2(OH)_{0.26}.24H_2O$ 04-011-1587 [10] were observed at minor levels. A number of unmatched peaks were observed indicating the presence of one or more additional impurity phases. A segment of the diffraction pattern of sample 1b is seen in red from 5°-18° 2-Theta. The green line shows the fitted background. The individual phases identified are indicated by a colour line group including the major levels of $NaAsO_2$ (blue) and $Na_2CO_3.H_2O$ (green) and minor levels of $Na_{6.26}(AsO_4)_2(OH)_{0.26}(H_2O)_{24}$ (pink) and $Na_2CO_3$ (brown). This indicates that the absence of sodium hydrogen carbonate in the manufacturing precludes the formation of the diarsenic tetraoxide $NaHAs_2O_4$.

Figure 9:
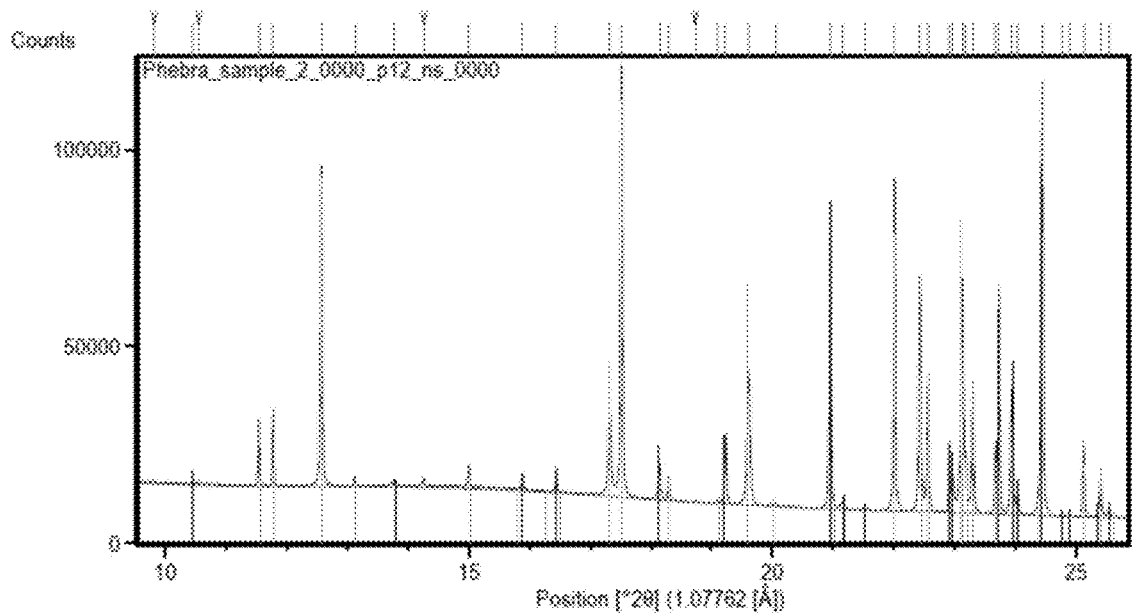
FIG. 9 is an X-ray powder diffraction pattern for sample 2, being a comparitor sample, from 9°-26° 2-Theta with overlayed search match results.

Finally, FIG. 9 shows a section of the diffraction pattern and the search/match results for sample 2, being the further sample formed without the use of sodium hydrogen carbonate. Three major phases were observed: $Na_2CO_3.H_2O$ 01-070-2148 [6], $NaAsO_2$ 04-016-1771 [4] and $Na_2CO_3$ 00-019-1130 [8]. Some unmatched peaks were observed indicating the presence of one or more additional impurity phases. FIG. 9 shows a segment of the diffraction pattern for sample 2 in red from 9°-26° 2-Theta. The green line shows the fitted background. The individual phases identified are indicated by a colour line group with the three major phases identified being: $NaAsO_2$ (green), $Na_2CO_3.H_2O$ (l.blue) and $Na_2CO_3$ (blue). As for sample 2, this reinforces that the absence of sodium hydrogen carbonate in the manufacturing precludes the formation of the diarsenic tetraoxide $NaHAs_2O_4$.

To be clear, FIGS. 5 to 7 therefore show 'zoomed-in' versions of the Powder Diffraction profiles of FIG. 4 (sample 3; two graphs showing lower, FIG. 5, and higher, FIG. 6, angle ranges) and FIG. 3 (sample 1a; FIG. 7 graph showing the lower angle range only). The vertical scales have been greatly increased to highlight the phases. The green/blue vertical lines on each plot indicate where peaks are expected (on the red trace) corresponding to the $NaHAs_2O_4$ crystal structure. Particularly for sample 3 (FIGS. 5 and 6) the presence of this phase is unmistakable; the green lines not only align with the position of the peak but their expected relative heights correspond to the data as well. The probability of a completely different crystalline phase matching with so many of the measured minor peaks as $NaHAs_2O_4$ is highly unlikely.

These results demonstrate that following the above procedure, with the important inclusion of the mixing with sodium hydrogen carbonate, results in formation of the diarsenic tetraoxide $NaHAs_2O_4$. This compound is generally formed in a mixture with remaining sodium carbonate and sodium hydrogen carbonate which is therefore included in the final composition which is used to fill the gelatin capsule. The sodium carbonate and sodium hydrogen carbonate provide advantages as described herein while the $NaHAs_2O_4$ is the 'active' delivery form for the therapeutically active arsenic ion.

Dissolution Studies

Comparative dissolution testing with arsenic trioxide was performed by the applicant and disclosed in their PCT application published as WO 2016/119019, the contents of which is hereby incorporated by reference in its entirety. In brief, even dissolution attempts at relatively high pH left only about 25% to 59% of the arsenic trioxide dissolved after 20 min. Even the use of 0.1 M NaOH required 15-20 min for complete dissolution. The present diarsenic tetraoxide compound provides an advantageous approach with the creation of an alternative and faster dissolving arsenic compound which drives greater blending of the capsule contents rapidly in the stomach chyme.

Dissolution in Simulated Gastric Solution

Simulated gastric solution was prepared containing 2 g NaCl, 7 ml of 37% HCl and then made up to 1 L to approximately pH 1.2 with water. The gelatin capsule containing the $NaHAs_2O_4$ was added to 150 mL of the simulated gastric solution and stirred at 37° C. In less than or about one minute the capsule shell had dissolved and in less than or about 2 minutes the $NaHAs_2O_4$ contents had completely dissolved.

Dissolution experiments were carried out on $NaHAs_2O_4$ at 2 different pH levels. Firstly, simulated gastric fluid (pH 1.24) was used, then a near neutral solution at pH 6.5. Prior to addition of the capsules, 150 mls of the dissolution solution was heated to 37° C. and the solution contained a spin bar at a speed of 2. The appropriate capsule was then added. It was found that in generally in less than two minutes, in both dissolution mediums, the $NaHAs_2O_4$ powder was completely dissolved. The results are shown in table 3, below.

TABLE 3

Results of dissolution experiments for $NaHAs_2O_4$.

| Capsule Samples | Total capsule Weight (mg) | pH | Time until capsule opens | Time powder dissolved (including capsule opening time) |
|---|---|---|---|---|
| 10 mg | 320 | 1.24 | 35 sec | 1 min 32 sec |
| 10 mg Rpt | 325 | 1.24 | 40 sec | 1 min 45 sec |
| 1 mg | 320 | 1.24 | 1 min 4 sec | 2 min 5 sec |
| 1 mg Rpt | 322 | 1.24 | 52 sec | 1 min 56 sec |
| 10 mg | 327 | 6.5 | 55 sec | 1 min 45 sec |
| 10 mg Rpt | 329 | 6.5 | 50 sec | 1 min 50 sec |
| 1 mg | 320 | 6.5 | 50 sec | 1 min 38 sec |
| 1 mg Rpt | 322 | 6.5 | 45 sec | 1 min 58 sec |

One advantage of the present invention lies in ensuring both very rapid and complete dissolution of the diarsenic tetraoxide (preferably $NaHAs_2O_4$) in the stomach contents (chyme), which has a pH of about 1 in resting mode without food. This will ensure that the salt will form an arsenous acid and be readily available for absorption in the small intestine. If this rapid dissolution does not occur and the stomach contents pass into the small intestine, which has a pH of about 6, it is unlikely that the arsenic salt will dissolve and a proportion will therefore pass through to the faeces. The key in treating cancer patients with a solid oral delivery form is to have the bioequivalence over a 24 hour period be approximately the same as that of the liquid injection form. Any failure to obtain complete dissolution in the stomach will mean that this aim is not achieved. The present invention provides a diarsenic tetraoxide salt which satisfies this requirement in a surprisingly effective manner.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this patent specification is intended to embrace all alternatives, modifications and variations of the present invention that have been discussed herein, and other embodiments that fall within the spirit and scope of the above described invention.

In the claims which follow and in the preceding description of the invention, except where the context clearly requires otherwise due to express language or necessary implication, the word "comprise", or variations thereof including "comprises" or "comprising", is used in an inclusive sense, that is, to specify the presence of the stated integers but without precluding the presence or addition of further integers in one or more embodiments of the invention.

BIBLIOGRAPHY

[1] K. S. Wallwork, B. J. Kennedy & D. Wang, The high resolution powder diffraction beamline for the Australian Synchrotron, *AIP Conference Proceedings*, (2007) 879-882.

[2] Schmitt, B., Bronnimann, ch., Eikenberry, E. F., Gozzo, F., Hormann, C., Horisberger, R., Patterson, B. Nucl. Instrum. Methods Phys. Res. A, (2003) 501, 267-272.

[3] McMurdie H., Morris M., Evans E., Paretzkin B., Wong-Ng W., Hubbard C., Powder Diffr. (1986) 1, 79.
[4] Lee C., Harrison W. T. A., Acta Crystallogr., Sec. C: Cryst. Struct. Commun. (2004) 60, m215.
[5] Fleet M. E., Liu X., Z. Kristallogr. (2009) 224, 144.
[6] Dickens B, Mauer F. A., Brown W E., J. Res. Natl. Bur. Stand. (1970) Sect A 74, 319.
[7] Pertlik F., Mitt. Oesterr. Mineral. Ges., (1986) 131, 7.
[8] Brouns E., Visser J. W. and de Wolff P. M., *Acta Cryst.* (1964). 17, 614.
[9] Sheldrick W. S, Hausler H. J. Z, Anorg. Allg. Chem. (1987) 549, 177, 1.

The invention claimed is:

1. A solid oral pharmaceutical composition comprising an alkali metal and/or an alkaline earth metal diarsenic (III) tetraoxide and a pharmaceutically acceptable excipient.

2. The composition of claim 1 wherein the alkali metal and/or the alkaline earth metal diarsenic (III) tetraoxide is of the formula $MHAs_2O_4$ wherein M is a metal with a valency of +1.

3. A pharmaceutical composition comprising a diarsenic tetraoxide of the formula $MHAs_2O_4$ wherein M is a metal with a valency of +1, and a pharmaceutically acceptable excipient.

4. The composition of claim 1 wherein the alkali metal and/or the alkaline earth metal diarsenic (III) tetraoxide is of the formula $NaHAs_2O_4$.

5. The composition of claim 1 further comprising one or more of a drying agent, a disintegrant and a dispersant.

6. The composition of claim 5 wherein the drying agent, disintegrant or dispersant is a bicarbonate and/or a carbonate compound.

7. The composition of claim 6 wherein the disintegrant or dispersant is selected from the group consisting of sodium bicarbonate, sodium carbonate, potassium carbonate, potassium bicarbonate, calcium carbonate, magnesium carbonate and magnesium bicarbonate, or a combination thereof.

8. The composition of claim 1 wherein the composition is in the form of a tablet, granule or capsule.

9. A method of treating cancer in a patient, wherein treatment comprises the step of orally administering the diarsenic tetraoxide of claim 1 to the patient, thereby treating the cancer, wherein said treatment alleviates the cancer, alleviates the symptoms of cancer and/or places the patient in a state of remission.

10. The method of claim 9 wherein the cancer is selected from a haematological malignancy, a solid tumour and a lymphoma.

11. The method of claim 9 wherein the cancer is selected from the group consisting of acute lymphoblastic leukaemia (ALL), acute lymphoblastic B-cell leukaemia, acute lymphoblastic T-cell leukaemia, acute myeloblastic leukaemia (AML), acute promyelocytic leukaemia (APL), acute monoblastic leukaemia, acute erythroleukemic leukaemia, acute megakaryoblastic leukaemia, acute myelomonocytic leukaemia, acute undifferentiated leukaemia, chronic myelocytic leukaemia, myelodysplastic syndrome (MDS) and chronic lymphocytic leukaemia.

12. The method of claim 11 wherein the cancer is acute promyelocytic leukaemia (APL).

13. The method of claim 12 wherein the cancer is multiple myeloma.

14. The method of claim 9 wherein the diarsenic tetraoxide is administered as part of a combination therapy.

15. A method of delivering a therapeutically effective amount of an arsenic ion to a patient including the step of administering to the patient an appropriate amount of a composition comprising the diarsenic tetraoxide as defined in claim 1.

16. A solid oral pharmaceutical composition comprising a diarsenic tetraoxide of the formula $MHAs_2O_4$ wherein M is a metal with a valency of +1.

17. A method of treating cancer in a patient wherein treatment comprises the step of orally administering the diarsenic tetraoxide of claim 3 to the patient, thereby treating the cancer, wherein said treatment alleviates the cancer, alleviates the symptoms of cancer and/or places the patient in a state of remission.

* * * * *